(12) United States Patent
Alksnis

(10) Patent No.: US 6,676,172 B2
(45) Date of Patent: Jan. 13, 2004

(54) ANESTHETIC GAS VAPORIZER WITH A CONNECTION ARRANGEMENT FOR A COLLAR-EQUIPPED GAS BOTTLE

(75) Inventor: Ivars Alksnis, Trangsund (SE)

(73) Assignee: Siemens-Elema AB, Solna (SE)

( * ) Notice: Subject to any disclaimer, the term of this patent is extended or adjusted under 35 U.S.C. 154(b) by 10 days.

(21) Appl. No.: 10/025,048

(22) Filed: Dec. 17, 2001

(65) Prior Publication Data
US 2002/0088461 A1 Jul. 11, 2002

(30) Foreign Application Priority Data
Dec. 19, 2000 (SE) ............................................. 0004701

(51) Int. Cl.[7] .............................................. F16L 39/00
(52) U.S. Cl. .......................... 285/319; 285/308; 215/43
(58) Field of Search ................................. 285/305, 308, 285/319, 321; 215/43, 386

(56) References Cited

U.S. PATENT DOCUMENTS

| 1,369,687 | A | * | 2/1921 | Martin | 285/317 |
|---|---|---|---|---|---|
| 1,582,681 | A | * | 4/1926 | Hammer | 215/43 |
| 3,453,005 | A | * | 7/1969 | Foults | 285/82 |
| 3,945,617 | A | * | 3/1976 | Callery | 366/347 |
| 4,524,995 | A | * | 6/1985 | Bartholomew | 285/54 |
| 4,721,331 | A | * | 1/1988 | Lemelshtrich | 285/305 |
| 4,803,053 | A | * | 2/1989 | Williamson | 422/101 |
| 4,884,829 | A | * | 12/1989 | Funk et al. | 285/24 |
| 5,048,874 | A | * | 9/1991 | Ohlsson | 285/307 |
| 5,378,024 | A | * | 1/1995 | Kumagai et al. | 285/39 |
| 5,536,047 | A | * | 7/1996 | Detable et al. | 285/39 |
| 5,653,475 | A |   | 8/1997 | Scheyhing et al. | |
| 5,687,777 | A |   | 11/1997 | Dobson et al. | |
| 6,149,206 | A | * | 11/2000 | DiRocco | 285/305 |
| 6,186,180 | B1 | * | 2/2001 | Moller et al. | 138/89 |
| 6,231,084 | B1 | * | 5/2001 | Hester et al. | 285/23 |
| 6,371,528 | B1 | * | 4/2002 | Kimura | 285/305 |

FOREIGN PATENT DOCUMENTS

| FR | 1.398.823 |   | 4/1965 | |
| FR | 1.527.890 |   | 4/1968 | |
| GB | 570671 | * | 7/1945 | 285/321 |
| SE | 300 399 |   | 4/1968 | |

\* cited by examiner

Primary Examiner—Lynne H. Browne
Assistant Examiner—James M. Hewitt
(74) Attorney, Agent, or Firm—Schiff Hardin & Waite

(57) ABSTRACT

An anesthetic vaporizer has a receiving part devised for connection to a collar-equipped bottle, the receiving part having a locking device for locking/unlocking the bottle. Improved connection is achieved by providing the receiving part with a tubular section with a tube wall and an internal cavity, with a through opening arranged in the tube wall enabling the bottle's collar to move past the opening when the bottle is attached to the receiving part. The opening extends down at an angle to the center line of the tubular section, and the locking device has a resilient locking element partially arranged in the opening. The resilient locking element is devised to assume, in a passive state, a first position inside the internal cavity preventing the unimpeded passage of the bottle's collar and, when acted upon, to move downwards-outwards in the opening to a second position in the cavity allowing the unimpeded passage of the bottle's collar, and an opening arrangement is disposed, when actuated, to act on the resilient locking element.

4 Claims, 2 Drawing Sheets

ANESTHETIC GAS VAPORIZER WITH A CONNECTION ARRANGEMENT FOR A COLLAR-EQUIPPED GAS BOTTLE

BACKGROUND OF THE INVENTION

1. Field of the Invention

The present invention is directed to an anesthetic vaporizer having a connection arrangement allowing connection with a collar-equipped bottle, of the type having a locking device for locking the bottle in, and unlocking the bottle from, the connection arrangement.

2. Description of the Prior Art

Known anesthetic vaporizers usually contain a chamber for liquid anesthetic. Anesthetic can be dispensed from this chamber in a liquid or vaporized state in order to form, with other gases, a breathing gas for a patient. The chamber can be filled with anesthetic from a bottle via a filler connector. The bottle can be connected directly to the filler connector or by means of various adapters.

Use of the bottle as the chamber is also known. The bottle is then connected to the vaporizer the whole time anesthesia is induced.

Regardless of which of the above systems is used, reliable connection between the bottle and the vaporizer is essential. More specifically, reliable locking/unlocking of a collar-equipped bottle to a vaporizer should be possible.

SUMMARY OF THE INVENTION

An object of the present invention is to provide an anesthetic vaporizer of the type initially described that allows reliable and functional connection of a collar-equipped bottle to the anesthetic vaporizer.

This objective is achieved according to the invention in an anesthetic vaporizer wherein the collar-equipped part of the bottle passes through a resilient element during its connection to the vaporizer. During this passage, the resilient element is pushed aside by the collar. The resilient element then locks the bottle in the receiving part when the element, after collar passes, springs back and inserts itself between the collar and the opening of the receiving part. The bottle can subsequently be released by maneuvering a spreading arrangement that acts on the resilient element. The spreading arrangement also can be used when the bottle is being connected in order to facilitate passage of the collar past the resilient element.

The movement of the resilient element during the passage of the collar (or when the resilient means is acted upon by the opening spreading arrangement) is regulated by through which the resilient element enters the interior cavity of the receiving part. These openings extend downwardly at an angle to the receiving part's center line (the opening of the receiving part is assumed here to be "up").

DESCRIPTION OF THE PREFERRED EMBODIMENTS

Figure 1:
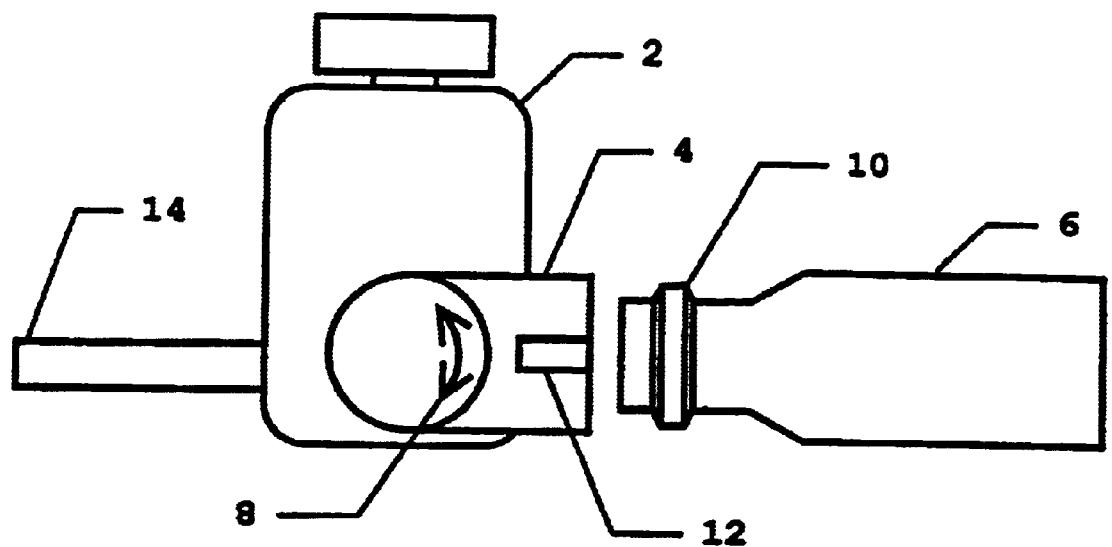
FIG. 1 shows an embodiment of an anesthetic vaporizer according to the invention.

An anesthetic vaporizer 2 is schematically depicted in FIG. 1. The anesthetic vaporizer 2 has a receiving part 4 for a bottle 6 containing anesthetic. The receiving part 4 can rotate, as designated by the arrow 8, to facilitate connection/disconnection of the bottle as well as the emptying of the contents of same into the vaporizer 2.

For connection, the bottle 6 is inserted into the receiving part 4. Connection can be made in order to fill a chamber (not shown) inside the vaporizer 2 with anesthetic, or the bottle 6 itself can serve as the anesthetic chamber. A collar 10 on the bottle 6 is employed for locking the bottle 6 in the receiving part 4. A spreading arrangement 12 is used for disconnecting the bottle 6. In instances when the bottle 6 does not have a collar or has a collar that does not fit the receiving part 4, an adapter with a suitably shaped collar 10 can be mounted on the bottle 6. The collar 10 in FIG. 1 represents both options.

A line 14 indicates that the vaporizer 2 dispenses anesthetic for end use by a patient. The manner in which dispensing is performed (whether the anesthetic is in liquid form, vaporized with a carrier gas or vaporized without a carrier gas etc.) is irrelevant to the present invention. The invention mainly relates to connection of the vaporizer 2 to the bottle 6 and to disconnection of the bottle 6.

Figure 2:
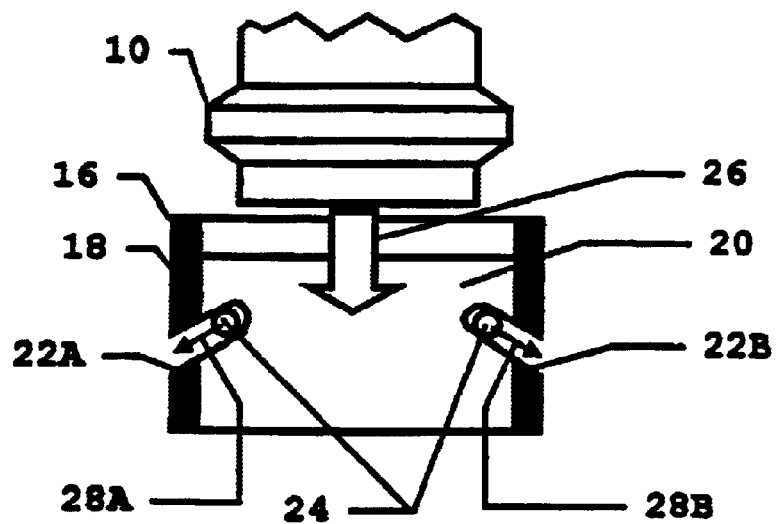
FIGS. 2–4 show an embodiment of the receiving part and the locking device in the anesthetic vaporizer according to FIG. 1.
Figure 3:
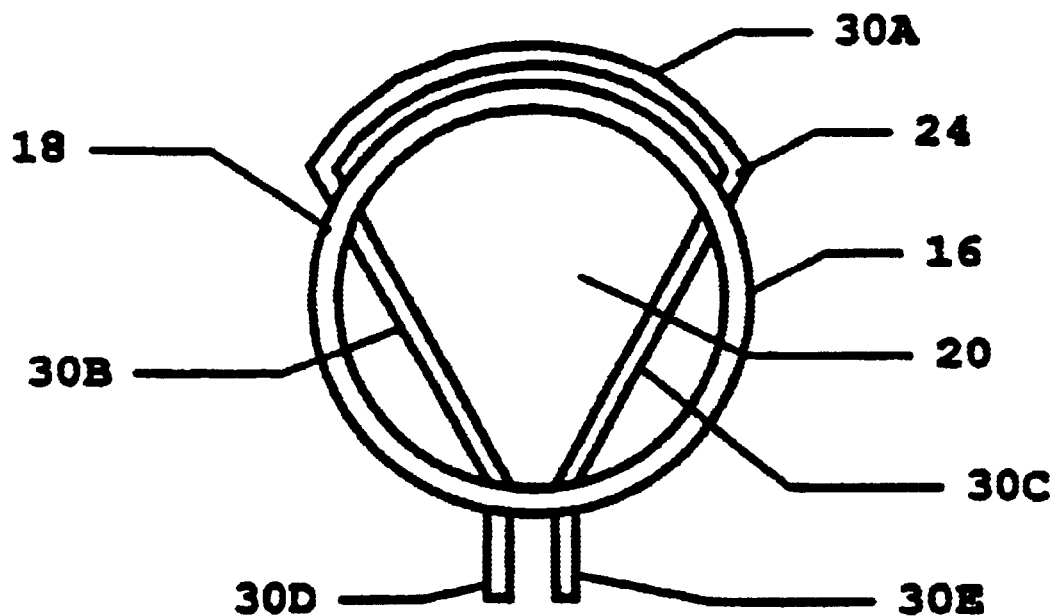
Figure 4:
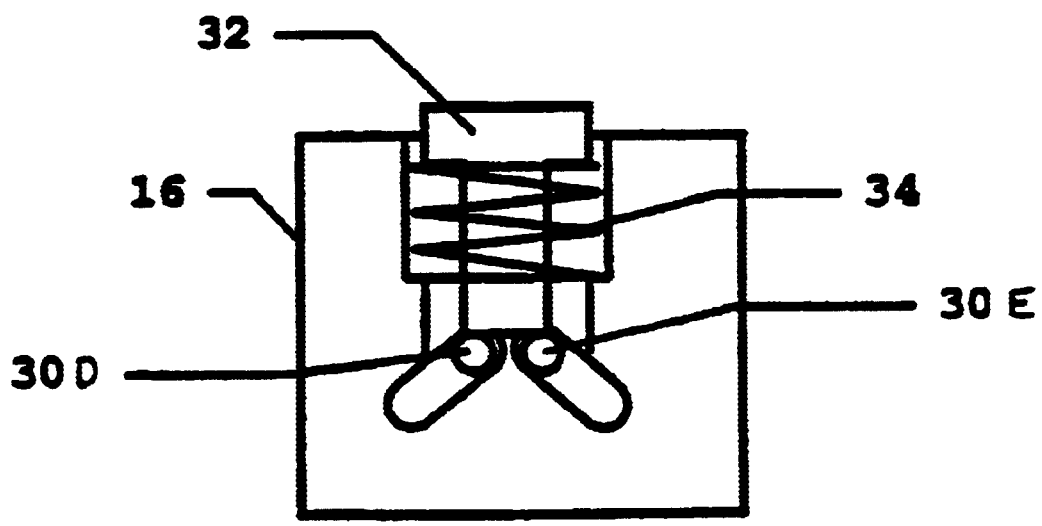

The following jointly refers to FIGS. 2–4, all of which show details of the way in which connection and locking/unlocking are devised.

The receiving part 4 has a tubular section 16 with a tube wall 18 and an internal cavity 20 (into which the collar-equipped 10 part of the bottle is inserted). The tube wall has two openings 22A, 22B devised for guiding a resilient locking element 24. When the collar 10 is inserted down into the internal cavity 20, as indicated by the arrow 26, the resilient locking element 24 is pushed down and outwardly, as indicated by the arrows 28A, 28B. The collar 10 will then be able to pass the locking element 24, which springs back (in the opposite direction in relation to the arrows 28A, 28B). Any attempt to withdraw the bottle in this position will cause the collar 10 to lock the bottle against the locking element 24 which is unable to move upwards.

The resilient element 24 is advantageously made of an essential flat component with a first section 30A which follows the shape of the tubular section 16, second and third essentially straight sections 30B, 30C which pass through the cavity 20, a first end 30D and a second end 30E which protrude outside the tubular section 16.

As a result of the shape of the ends 30D, 30E, a rod-like or shaft-like actuator 32 can be arranged on the exterior of the tubular section 16. When the actuator 32 is depressed, the ends 30D, 30E are pressed downwards/outwards, thereby enabling the collar 10 to move upwardly and pass the locking element 24. The bottle can then be removed from the receiving part 4. The actuator 32 is advantageously biased with a spring 34 so it rebounds to its original position when released. The spreading arrangement also can be used when the bottle is to be connected to the receiving part 4.

Other versions of the different components fall within the scope of the inventive concept. For example, the locking element 24 can be devised in various versions of the shape illustrated, more or fewer openings 22A, 22B can be devised in some other way (e.g. with a radial orientation), the rod can have another design (e.g. in which only the ends are pressed apart) or they can be arranged within the interior of the tubular section 16) etc.

Although modifications and changes may be suggested by those skilled in the art, it is the intention of the inventor to embody within the patent warranted hereon all changes and modifications as reasonably and properly come within the scope of his contribution to the art.

I claim:

1. A connection arrangement for a collar-equipped bottle in an anesthetic vaporizer, said connection arrangement comprising:

a receiving part having a tubular section with a tube wall and an interior cavity, said tube wall having a through opening therein adapted to allow a collar of a gas bottle to move through the opening when the bottle is inserted into said receiving part, said opening extending at an angle relative to a center line of said tubular section;

a locking device adapted to interact with the collar of the bottle as the bottle is inserted into said receiving part, said locking device comprising a resilient locking element having a circular arc and two radially disposed parallel ends connected thereto, said locking element partially disposed in said opening and assuming, in a passive state, a first position inside said interior cavity preventing unimpeded passage of said collar and, when acted upon, being axially downwardly and radially outwardly movable in said opening to a second position in said cavity allowing unimpeded passage of said collar past said locking element; and an actuatable spreading arrangement disposed for acting upon said locking element for, when actuated, spreading said resilient locking element to allow unimpeded passage of said collar therethrough.

2. A connection arrangement as claimed in claim 1 said ends of said locking element protrude from an exterior of said tube wall, and wherein said spreading arrangement comprises an actuator mounted for movement along said exterior of said tube wall parallel to said ends to act on said ends causing said ends to move axially downwardly and radially outwardly in said opening.

3. A connection arrangement as claimed in claim 1 wherein said resilient element has a portion thereof passing through said interior cavity which is substantially straight.

4. A connection arrangement as claimed in claim 1 further comprising an adapter for attachment to said bottle, said adapter carrying said collar thereon.

* * * * *